(12) United States Patent
Perroud et al.

(10) Patent No.: US 8,815,177 B2
(45) Date of Patent: Aug. 26, 2014

(54) METHODS AND DEVICES FOR IMMOBILIZATION OF SINGLE PARTICLES IN A VIRTUAL CHANNEL IN A HYDRODYNAMIC TRAP

(75) Inventors: Thomas D. Perroud, San Jose, CA (US); Kamlesh D. Patel, Dublin, CA (US)

(73) Assignee: Sandia Corporation, Albuquerque, NM (US)

(*) Notice: Subject to any disclaimer, the term of this patent is extended or adjusted under 35 U.S.C. 154(b) by 612 days.

(21) Appl. No.: 12/812,974

(22) PCT Filed: Jan. 21, 2009

(86) PCT No.: PCT/US2009/031515
§ 371 (c)(1), (2), (4) Date: Jul. 15, 2010

(87) PCT Pub. No.: WO2009/131722
PCT Pub. Date: Oct. 29, 2009

(65) Prior Publication Data
US 2011/0028351 A1    Feb. 3, 2011

Related U.S. Application Data

(60) Provisional application No. 61/062,401, filed on Jan. 24, 2008, provisional application No. 61/062,545, filed on Jan. 24, 2008, provisional application No. 61/142,780, filed on Jan. 6, 2009.

(51) Int. Cl.
*G01N 1/40* (2006.01)
*B01L 3/00* (2006.01)

(52) U.S. Cl.
USPC ..................................... 422/503; 422/68.1

(58) Field of Classification Search
USPC ............... 422/68.1, 500, 501, 502, 503, 504; 436/174, 177, 183
See application file for complete search history.

(56) References Cited

U.S. PATENT DOCUMENTS

| | | | |
|---|---|---|---|
| 5,654,238 A | 8/1997 | Cronin et al. | |
| 6,432,290 B1 | 8/2002 | Harrison et al. | |
| 6,629,820 B2 | 10/2003 | Kornelsen | |

(Continued)

FOREIGN PATENT DOCUMENTS

| | | |
|---|---|---|
| JP | 2006-181670 | 7/2006 |
| JP | 2007-098488 | 4/2007 |

(Continued)

OTHER PUBLICATIONS

International Search Report for Application No. PCT/US2009/031515 mailed Oct. 28, 2009.

(Continued)

*Primary Examiner* — Christopher A Hixon
(74) *Attorney, Agent, or Firm* — Suzannah K. Sundby

(57) ABSTRACT

Disclosed herein are methods of immobilizing a particle which comprise focusing the flow of a sample fluid containing the particle into a virtual channel which flows towards an unoccupied hydrodynamic trap in a microfluidic channel such that the particle flows into the hydrodynamic trap and becomes immobilized therein. Also disclosed are microfluidic devices which comprise at least one microchannel having at least one hydrodynamic trap, at least one focusing fluid inlet, said focusing fluid inlet is upstream of the hydrodynamic trap such that a focusing fluid introduced therein results in a virtual channel of a sample fluid when present which preferentially flows toward the hydrodynamic trap.

8 Claims, 14 Drawing Sheets

(56) References Cited

U.S. PATENT DOCUMENTS

| | | | |
|---|---|---|---|
| 6,632,619 | B1 | 10/2003 | Harrison et al. |
| 6,706,203 | B2 | 3/2004 | Barth et al. |
| 6,824,663 | B1 | 11/2004 | Boone |
| 6,833,542 | B2 | 12/2004 | Wang et al. |
| 6,875,619 | B2 | 4/2005 | Blackburn |
| 6,900,021 | B1 | 5/2005 | Harrison et al. |
| 7,077,175 | B2 | 7/2006 | Yin et al. |
| 7,094,354 | B2 | 8/2006 | Pugia et al. |
| 7,125,667 | B2 | 10/2006 | Blumenfeld et al. |
| 7,157,274 | B2 | 1/2007 | Böhm et al. |
| 7,171,975 | B2 | 2/2007 | Moon et al. |
| 7,220,592 | B2 | 5/2007 | Rakestraw et al. |
| 7,244,961 | B2 | 7/2007 | Jovanovich et al. |
| 7,296,592 | B2 | 11/2007 | Rehm et al. |
| 7,312,611 | B1 | 12/2007 | Harrison et al. |
| 7,351,315 | B2 | 4/2008 | Klocke et al. |
| 2002/0197167 | A1 | 12/2002 | Kornelsen |
| 2003/0178075 | A1 | 9/2003 | Moon et al. |
| 2003/0217923 | A1 | 11/2003 | Harrison et al. |
| 2004/0178071 | A1 | 9/2004 | Harrison et al. |
| 2004/0209354 | A1 | 10/2004 | Mathies et al. |
| 2004/0235181 | A1 | 11/2004 | Arnold et al. |
| 2004/0265172 | A1 | 12/2004 | Pugia et al. |
| 2005/0009101 | A1 | 1/2005 | Blackburn |
| 2005/0050767 | A1 | 3/2005 | Hanson et al. |
| 2005/0207940 | A1 | 9/2005 | Butler et al. |
| 2005/0224134 | A1 | 10/2005 | Yin et al. |
| 2006/0014360 | A1 | 1/2006 | Matsumoto |
| 2006/0060767 | A1 | 3/2006 | Wang et al. |
| 2006/0222635 | A1 | 10/2006 | Centanni et al. |
| 2007/0099289 | A1 | 5/2007 | Irimia et al. |
| 2007/0170056 | A1 | 7/2007 | Arnold et al. |
| 2007/0243523 | A1 | 10/2007 | Ionescu-Zanetti et al. |
| 2007/0248958 | A1 | 10/2007 | Jovanovich et al. |
| 2007/0272309 | A1 | 11/2007 | Rehm et al. |
| 2008/0014576 | A1 | 1/2008 | Jovanovich et al. |
| 2008/0020368 | A1 | 1/2008 | Yang et al. |
| 2008/0020370 | A1 | 1/2008 | Philpott et al. |
| 2008/0138848 | A1 | 6/2008 | Li et al. |
| 2008/0179180 | A1 | 7/2008 | McHugh et al. |
| 2008/0182136 | A1 | 7/2008 | Arnold et al. |

FOREIGN PATENT DOCUMENTS

| | | |
|---|---|---|
| WO | 03/044164 A2 | 5/2003 |
| WO | 03/044164 A3 | 5/2003 |
| WO | 03/068672 A2 | 8/2003 |
| WO | 2003/068672 A3 | 8/2003 |
| WO | 2005/001896 A2 | 1/2005 |
| WO | 2005/001896 A3 | 1/2005 |
| WO | 2005/028108 | 3/2005 |
| WO | 2005/096751 A2 | 10/2005 |
| WO | 2005/096751 A3 | 10/2005 |
| WO | 2006/007701 A1 | 1/2006 |
| WO | 2006/019500 A2 | 2/2006 |
| WO | 2006/019500 A3 | 2/2006 |
| WO | 2006/032044 A2 | 3/2006 |
| WO | 2006/032044 A3 | 3/2006 |
| WO | 2007/087632 A2 | 8/2007 |
| WO | 2007/087632 A3 | 8/2007 |

OTHER PUBLICATIONS

International Search Report for Application No. PCT/US2009/031516 mailed Oct. 30, 2009.

Tan et al., "A trap-and-release integrated microfluidic system for dynamic microarray applications", PNAS, Jan. 2007, 104(4), pp. 1146-1151.

Huh et al., "Gravity-Driven Microfluidic Particle Sorting Device with Hydrodynamic Separation Amplification", Anal. Chem., 2007, 79, 1369-1376.

Ohta et al., "Dynamic Cell and Microparticle Control via Optoelectronic Tweezers", Journal of Microelectromechanical Systems, Jun. 2007, vol. 16, No. 3, pp. 491-499.

Fu et al., "Electrokinetically driven microflow cytometers with integrated fiber optics for on-line cell/particle detection", Analytica Chimica Acta 507, 2004, pp. 163-169.

Shah et al., "A microfluidic system to capture single cells", Jun. 21 2007, MIC—Depart. of Micro and Nanotechnology, DTU bldg. 345 east Technical University of Denmark, DK-2800 Kongens Lyngby, Denmark, pp. 1-5.

Shuler et al., "Hydrodynamic Focusing and Electronic Cell-Sizing Techniques", Applied Microbiology, Sep. 1972, 24(3), pp. 384-388.

Tu et al., "Microfluidic cell analysis and sorting using photonic forces", Optical Trapping and Optical Micromanipulation, Proceedings of SPIE, 2004 vol. 5514, pp. 774-785.

Wang et al., "Microfluidic sorting of mammalian cells by optical force switching", Nature Biotechnology, Jan. 2005, vol. 23, No. 1, pp. 83-87.

Di Carlo et al., "Continuous inertial focusing, ordering, and separation of particles in microchannels", PNAS, Nov. 27, 2007, vol. 104, No. 48, pp. 18892-18897.

Williams et al., Etch Rates for Micromachining Processing—Part II, Journal of Microelectromechinical Systems, Dec. 2003, vol. 12, No. 6, pp. 761-778.

Fu et al., "A high-discernment microflow cytometer with microweir structure", Electrophoresis, 2008, 29, pp. 1874-1880.

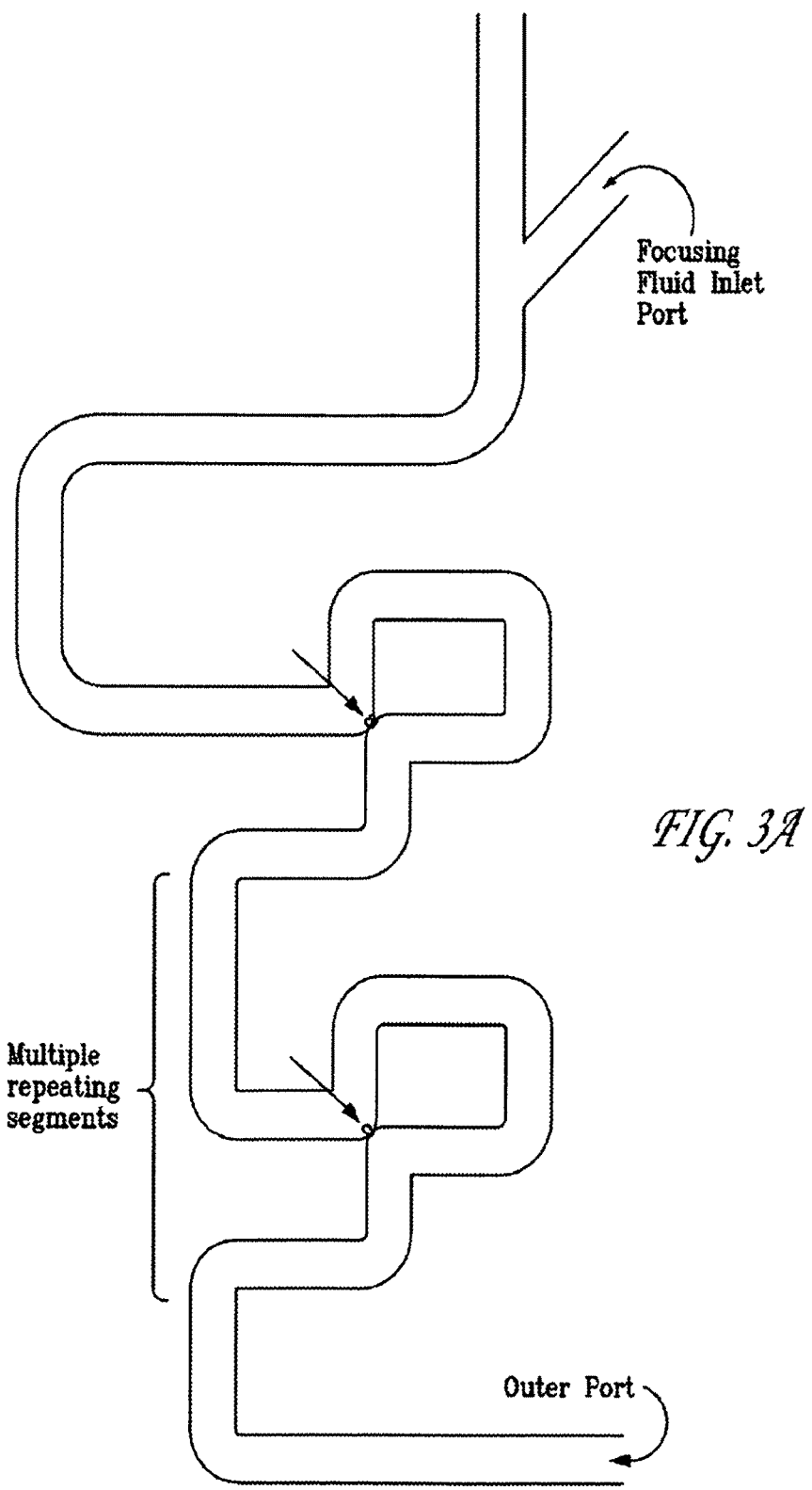

2nd cell

METHODS AND DEVICES FOR IMMOBILIZATION OF SINGLE PARTICLES IN A VIRTUAL CHANNEL IN A HYDRODYNAMIC TRAP

CROSS-REFERENCE TO RELATED APPLICATIONS

This application claims the benefit of U.S. Patent Application Ser. No. 61/062,401, filed 24 Jan. 2008, U.S. Patent Application Ser. No. 61/062,545, filed 24 Jan. 2008, and U.S. Patent Application Ser. No. 61/142,780, filed 6 Jan. 2009, all of which are herein incorporated by reference in their entirety.

ACKNOWLEDGEMENT OF GOVERNMENT SUPPORT

Employees of Sandia National Laboratories made this invention. The government has certain rights in the invention.

BACKGROUND OF THE INVENTION

1. Field of the Invention

The present invention generally relates to methods and devices for sorting particles in a fluid such that a single particle may be isolated and analyzed.

2. Description of the Related Art

Microfluidic devices have a unique and distinct advantage for manipulating and analyzing a single particle, such as a biological cell, microorganism or a biomolecule like a protein, polynucleotide, polysaccharide, lipid, and the like.

Several microfluidic techniques have been developed to manipulate, e.g., transport and immobilize, individual cells in an array, such as (1) dielectrophoretic trapping, which confines cells in a potential well created by electrodes but involves complicated chip fabrication processes; (2) holographic optical trapping limited by the induced photodamage on the cell after an extended period of time; (3) microwell trapping characterized by a random and slow cell loading step given its reliance on gravitational forces. See e.g. Gascoyne et al. (2002) J. Electrophoresis 23:1973-1983; Fuchs et al. (2006) Lab on a Chip 6: 121-126; Voldman et al. (2002) Anal. Chem. 74:3984-3990; Neuman et al. (1999) Biophysical J. 77:2856-2863; Rettig & Folch (2005) Anal. Chem. 77:5628-5634; and Wheeler et al. (2003) Anal. Chem. 75:3581-3586; Tan & Takeuchi (2007) PNAS 104(4):1146-1151, and Shah & Lange (2007) "A microfluidic system to capture single cells" available on the World Wide Web 2 (www2) at mic.dtu.dk/research/MIFTS/publications/3 week/Jun2007_CellCapture.pdf. Unfortunately, these prior art methods and devices for transporting and immobilizing a single particle for further analysis or processing often suffer from problems of poor efficiency of capture, clogging of the microfluidic channel, and low throughput of single particles.

Therefore, a need exists for methods and devices which have high efficiency and high throughput without clogging.

SUMMARY OF THE INVENTION

The present invention provides a method for immobilizing a single particle or a plurality of single particles, which may be the same or different. The method of the present invention comprises focusing the flow of a sample fluid containing the particle into a virtual channel which flows towards an unoccupied hydrodynamic trap in a microfluidic channel such that the particle flows into the hydrodynamic trap and becomes immobilized therein.

In some embodiments, the particle is directed towards a hydrodynamic trap by creating a virtual channel in a microchannel by introducing a focusing fluid such that the flow of the virtual channel is directed towards the trap. In these embodiments, a focusing fluid is used to hydrodynamically focus the flow of the sample fluid into the virtual channel.

In some embodiments, the center of mass of the particle is located in the virtual channel. In some embodiments, the virtual channel has a cross section having a width that is about the same as or bigger than the radius of the particle. In some embodiments, the virtual channel has a cross section having a width that is about the same as or bigger than the radius of the particle and the center of mass of the particle is located in the virtual channel.

In some embodiments, the flow stream of the sample fluid towards the unoccupied hydrodynamic trap is greater than the flow stream of the sample fluid which passes by the unoccupied hydrodynamic trap.

In some embodiments, the hydrodynamic trap is a cavity having a diameter of about 20 μm. In some embodiments, the hydrodynamic trap has a micropore. In some embodiments, a plurality of hydrodynamic traps which may be the same or different are employed.

In some embodiments, the focused flow may be subjected to secondary fluid focusing. In some embodiments, the secondary fluid focusing is conducted with a second focusing fluid which is the same or different from the first focusing fluid. In some embodiments, the secondary fluid focusing changes the dimensions of the virtual channel.

In some embodiments, particles of interest may be sorted or selected prior to focusing the sample fluid.

In some embodiments, the present invention provides a method of making an array of a plurality of particles each individually immobilized in a plurality of hydrodynamic traps which comprises immobilizing each particle in accordance with the present invention. In some embodiments, the present invention is directed to a single cell (particle) array made by immobilizing the cells in accordance with the present invention.

In some embodiments, the present invention provides a microfluidic device which comprises at least one microchannel having at least one hydrodynamic trap, at least one focusing fluid inlet, said focusing fluid inlet is upstream of the hydrodynamic trap such that a focusing fluid introduced therein results in a virtual channel of a sample fluid when present which preferentially flows toward the hydrodynamic trap. In some embodiments, the microfluidic device according to the present invention may have one or more sets of hydrodynamic traps in series, in parallel, or a combination thereof. In some embodiments, the microfluidic device comprises at least one secondary fluid inlet. In some embodiments, one or more hydrodynamic traps may have one or more trapping agents. In some embodiments, one hydrodynamic trap may have two or more different trapping agents. In some embodiments, one hydrodynamic trap may have one type of trapping agent and another hydrodynamic trap may have second trapping agent that is different from the first.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 3A schematically shows an example of a microchannel configuration for hydrodynamic confinement after fluid focusing in accordance with the present invention. The unlabeled arrows point to hydrodynamic traps, each with a single particle immobilized therein.

In FIG. 7, inset (A) shows a cell (e.g. a macrophage was used as the particle) of interest initially detected by forward scattering, inset (B) shows the cell entering the near-infrared laser sorting region, inset (C) shows the cell being deflected by optical gradient forces, inset (D) shows the cell being released in a different laminar flow stream, and inset (E) shows the binning of the cell into another microchannel.

FIGS. 1-12 show fluorescently labeled single cells trapped at each hydrodynamic trap.

FIG. 9 is an SEM micrograph of a hydrodynamic trap of a single cell array (SCA) at a magnification of 200×. The inset is a 1000× magnification.

FIG. 10A shows a first cell is located in the middle of the channel.

FIG. 10B shows the first cell bypasses the hydrodynamic trap and is pulled towards the interior channel wall.

FIG. 10C shows the first cell is closer to the interior channel wall as compared to a second subsequent particle.

FIG. 10D shows the first cell is pushed back to the middle of the channel after bypassing the back of the trap while the second cell is pulled towards the interior channel wall.

FIG. 12 is a compilation of images from 12 sequential traps according to the present invention.

DETAILED DESCRIPTION OF THE INVENTION

Figure 1A:
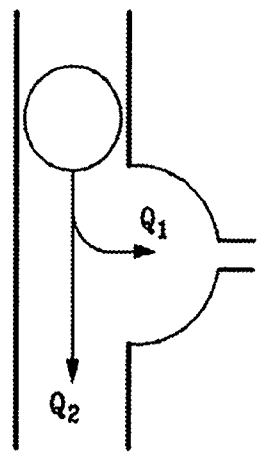
FIG. 1A schematically shows the hydrodynamic forces of a hydrodynamic trap according to prior art methods and devices.

The present invention relates to methods and devices for immobilizing a single particle using hydrodynamic confinement in conjunction with fluid focusing. As disclosed herein, an individual particle of interest in a fluid sample in a microfluidic channel becomes immobilized in a microfluidic trap located in the microfluidic channel by hydrodynamic confinement. A fluid focusing method known in the art, such as hydrodynamic focusing, is used to focus the fluid sample and direct the flow of the focused fluid to improve the efficiency of the hydrodynamic confinement of the particle of interest while reducing the risk of clogging.

As used herein, "channel" refers to a structure wherein a fluid may flow. A channel may be a capillary, a conduit, a strip of hydrophilic pattern on an otherwise hydrophobic surface wherein aqueous fluids are confined, and the like. As used herein, "microfluidic" refers to a system or device having one or more fluidic channels, conduits or chambers that are generally fabricated at the millimeter to nanometer scale. Thus, the "microfluidic channels" or alternatively referred to herein as "microchannels" of the present invention generally have cross-sectional dimensions ranging from about 10 nm to about 1 mm.

As used herein, a "particle" may be natural or synthetic chemicals or biological entities. Chemicals and biological entities (biomolecules) include industrial polymers, powders, latexes, emulsions, colloids, environmental pollutants, pesticides, insecticides, drugs such as cocaine and antibiotics, magnetic particles, high-magnetic-permeability particles, metal ions, metal ion complexes, inorganic ions, inorganic ion complexes, organometallic compounds, metals including aluminum, arsenic, cadmium, chromium, selenium, cobalt, copper, lead, silver, nickel, and mercury, and the like, amino acids, peptides, proteins, glycoproteins, nucleotides, nucleic acid molecules, carbohydrates, lipids, lectins, cells, viruses, viral particles, bacteria, organelles, spores, protozoa, yeasts, molds, fungi, pollens, diatoms, toxins, biotoxins, hormones, steroids, immunoglobulins, antibodies, supermolecular assemblies, ligands, catalytic particles, zeolites, and the like, biological and chemical warfare agents, agents used in explosives, and the like.

As used herein, a "fluid" refers to a continuous substance that tends to flow and to conform to the outline of a container such as a liquid or a gas. Fluids include saliva, mucus, blood, plasma, urine, bile, breast milk, semen, water, liquid beverages, cooking oils, cleaning solvents, ionic fluids, air, and the like. Fluids can also exist in a thermodynamic state near the critical point, as in supercritical fluids. If one desires to test a solid sample for a given particle according to the present invention, the solid sample may be made into a fluid sample using methods known in the art. For example, a solid sample may be dissolved in an aqueous solution, ground up or liquefied, dispersed in a liquid medium, melted, digested, and the like. Alternatively, the surface of the solid sample may be tested by washing the surface with a solution such as water or a buffer and then testing the solution for the presence of the given particle.

Hydrodynamic Confinement

The principle of hydrodynamic confinement is based upon a hydrodynamic trap which is generally a cavity, such as a dam structure, an intersection of a smaller channel, a gap, a pore, or small channel, and the like, in a fluidic channel. The cavity is in fluidic communication with a different part of the same fluidic channel or a second fluidic channel when it is unoccupied. As used herein, "pore" is a hole, an opening or an interstitial space in an object, such as the substrate of the present invention, through which a fluid can flow. In some embodiments, the pore is a micropore. As used herein, a "micropore" is a pore having a size ranging from about 100 μm to about 1 μm and preferably about 40 μm to about 5 μm.

When a particle in a fluid sample is in the vicinity of an unoccupied hydrodynamic trap, the particle becomes immobilized in the trap. Once the cavity of the hydrodynamic trap is occupied, the fluid sample is redirected towards the next unoccupied hydrodynamic trap. See e.g. Tan & Takeuchi (2007) PNAS USA 104:1146-1151, which is herein incorporated by reference. Generally, prior art methods of hydrodynamic confinement flow particles in a sample fluid to a hydrodynamic trap in a random and unbiased manner.

FIG. 1A schematically shows the principle of hydrodynamic confinement according to methods and devices of the prior art. $Q_1$ is the fluid flow path through the cavity prior to the cavity being occupied by a particle. $Q_2$ is the fluid flow path around the cavity prior to the cavity being occupied by a particle. Once a particle, such as a cell, is trapped in the cavity, the particle acts as a plug, thereby dramatically increasing the fluidic resistance along the fluid flow path $Q_1$ which results in the rest of the fluid sample being redirected along fluid flow path $Q_2$ which bypasses the occupied cavity. See e.g. Di Carlo et al. (2006) Lab on a Chip 6:1445-1449; Yang et al. (2002) Anal Chem. 74:3991-4001; Yang et al. (2004) Lab on a Chip 4:53-59; and Lee et al. (2005) Applied Physics Letters 86:223902 which are herein incorporated by reference.

The preferential pattern of initial or pre-trapping flow streams ($Q_1 \gg Q_2$) is achieved by decreasing the fluidic resistance of $Q_1$ flow path compared to $Q_2$ flow path. Since the cross section of $Q_1$ flow path is smaller than $Q_2$ flow path in order to act as a hydrodynamic trap, the fluidic resistance of $Q_2$ flow path is increased by restricting its width to the smallest dimension possible (i.e. diameter of the particle of interest) and increasing its length. However, as the width of the main channel decreases, the susceptibility of $Q_2$ flow path to clogging increases. Conversely, as the width of $Q_2$ flow path increases, the likelihood that the particles flow past the hydrodynamic trap without becoming immobilized increases. Additionally, the particles have to be homogenous in size in order for adequate trapping to occur.

The present invention addresses the prior art problems by avoiding clogging while maintaining high trapping efficiency by coupling hydrodynamic confinement with fluid focusing.

Fluid Focusing

Figure 1B:
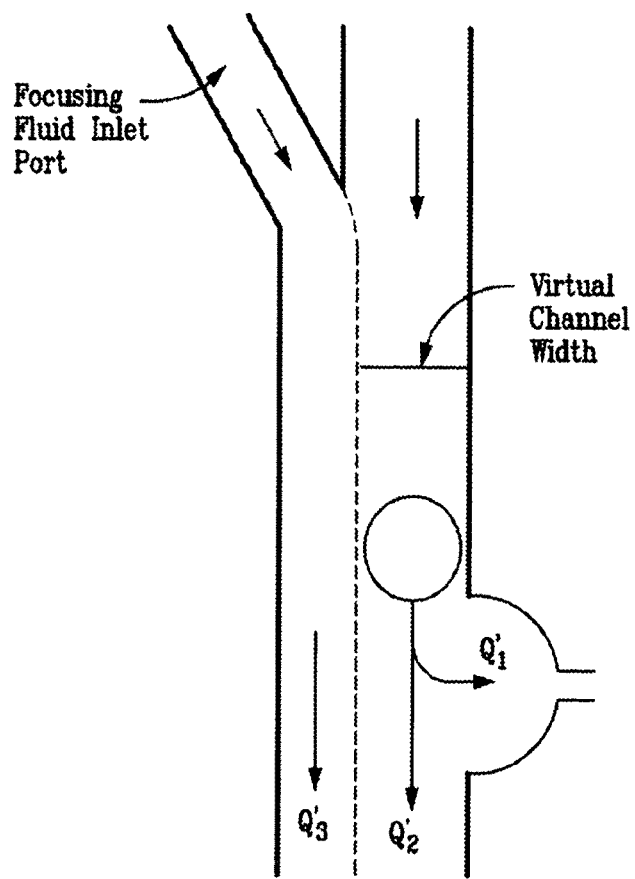
FIG. 1B schematically shows the hydrodynamic forces of a hydrodynamic trap according to the present invention.

The present invention solves the problems of the prior art by using fluid focusing, such as hydrodynamic focusing, to form a virtual channel made of a focused sample fluid. As used herein, a "virtual channel" refers to a fluid flow in a microchannel wherein at least one of its boundaries is not defined by a wall of the microchannel. The focused sample fluid flows towards $Q_1'$ as shown in FIG. 1B. A particle in the focused sample fluid will become immobilized in the hydrodynamic trap. Once the trap is occupied then subsequent particles will be directed along $Q_2'$. As provided herein, fluid focusing allows the dimensions of a microchannel to be significantly larger than the particle of interest and yet result in a desired flow rate ratio, $Q_1'/Q_2'$, that provides highly efficient hydrodynamic confinement because nearly all of flow from the virtual channel is directed towards flow path $Q_1'$.

Prior to the present invention, prior art microfluidic methods and devices have employed the principle of hydrodynamic focusing for sorting particles which involve detecting particles suspended in a fluid and then deflecting particles of interest towards a second channel according to a given characteristic, such as optical absorption, fluorescent intensity, size, or the like. See, for example, Shuler et al. (1972) Appl. Microbiol. 24(3):384-388, U.S. Pat. Nos. 4,175,662, 3,984,307, 4,756,427, 5,837,200, and 7,157,274, which are herein incorporated by reference. The prior art methods and devices employing hydrodynamic focusing are only concerned with directing a particle of interest to flow to a second channel for further processing.

The prior art methods and devices have not employed hydrodynamic focusing to provide a focused fluid flow within a microchannel in conjunction with further processing, such as hydrodynamic confinement, within the same microchannel because diffusion and mixing due to inertial forces, such as those caused by numerous turns, in a microfluidic channel was expected to alter the focused fluid flow such that only one fluid flow stream would remain after traveling a small distance, e.g. about 650 μm, flowing through a few number of turns, e.g. about 8 turns, or both. See e.g. Shediac et al. (2001) J Chromatography A 925(1): 251-263, which is herein incorporated by reference. In fact, Di Carlo et al. show that particles migrate across fluid streamlines in microchannels and that various geometries of microchannels bias the particle flow to particular equilibrium paths. See Di Carlo et al. (2007) PNAS USA 104(48):18892-18897, which is herein incorporated by reference.

However, it was unexpectedly found that the focused flow of a sample fluid could be sufficiently maintained in order to sequentially immobilize a plurality of single particles, such as cells, in subsequent hydrodynamic traps with a high degree of efficiency. As provided herein, experiments show that a focused fluid flow can be maintained for a distance up to about 30 mm and up to 200 geometrical turns.

Thus, the present invention employs fluid focusing to create at least one virtual channel in a microchannel, wherein the virtual channel comprises a sample fluid containing a particle of interest, and virtual channel is directly adjacent to one or more hydrodynamic traps in the microchannel. In some embodiments, at least one of the boundaries of the virtual channel is defined by a focusing fluid flow. The focusing fluid flow may have the same, faster, slower, or zero average fluid velocity as compared to that of the sample fluid flow (the fluid flow of the virtual channel). The focusing fluid may be the same or different from the sample fluid.

The width of the virtual channels according to the present invention may be manipulated or controlled to be of a desired size using methods known in the art. In some embodiments, however, the virtual channel comprising the sample fluid containing a particle of interest has a cross section which is about the same size as that of the particle of interest. It is known that in pressure-driven flow in a tube of a defined cross-sectional area, there is a velocity profile distribution that approximates a parabolic profile with the fastest or high velocity flow in the center. Flows near the side walls approach a zero velocity. Hence, in these embodiments, the effective flow rate of the defined of the virtual channel is the flow rate, $Q_1'+Q_2'$, and if near a side wall, effectively lower than the flow rate of the main channel, $Q_1'+Q_2'+Q_3'$.

In some embodiments, the effective area of the cross section of the virtual channel comprising the sample fluid may range from about 1.1 to about 1000 fold, preferably about 5 to about 20 fold, and more preferably about 9 to about 10 fold, larger than the cross-sectional area of the particle of interest. In some embodiments, the present invention provides $Q_1'/Q_2'$, ratio that ranges from 0.01 to 99, preferably about 1 to about 10, and more preferably about 3 to about 4.

As exemplified herein, hydrodynamic focusing was used to form the virtual channel made of a focused sample fluid. In some embodiments, the focusing fluid and the sample fluid are immiscible in each other. For example, the focusing fluid may be hydrophobic and the sample fluid may be hydrophilic. Alternatively, the focusing fluid and the sample fluid may be different states of matter. For example, the sample fluid may be a liquid and the focusing flow may be a gas that is an inert gas with respect to the sample fluid and the particles of interest.

Other methods known in the art may be used to focus a sample fluid into a virtual channel. For example, a fluid containing ions and the particles of interest may be electrokinetically driven along a microchannel such that a virtual channel within the microchannel is formed. Magnetohydrodynamics may be used to direct a fluid which experiences a dipole moment along a microchannel such that a virtual channel within the microchannel is formed. Dielectrophoretic forces may be used to focus a fluid in a microchannel in the form of a virtual channel. In these alternative embodiments, the fluid being driven along the microchannel may be either a sample fluid or a focusing fluid. It should be noted that in these alternative embodiments, the focusing fluid need not be a liquid, but may be a gas such as an inert gas or air.

In some embodiments, the walls of a microchannel may be treated using methods known in the art to optimize or modify the laminar flow of a fluid therein. For example, the native surface of glass can be modified to be hydrophobic using silane chemistry according to methods known in the art. An example of the numerous mono- and multi-layer hydrophobic coatings that can be used in accordance with methods known in the art is trimethoxysilane, which results in a surface that is hydrophobic. At high pH solutions, the native surface of materials like glass exhibits a negative charge. Thus, in some embodiments, the surface of a microchannel may be modified to result in a positive surface charge using ion-masking buffers (e.g. TRIS, CTAB, HEPES) using methods known in the art, or nanoparticles with a positive surface charge. See e.g. U.S. Pat. No. 7,297,246, which is herein incorporated by reference. In some embodiments, permanent and temporary coatings of biological proteins (e.g. serum albumin) or photopolymerizable polymers (e.g. metharcylates) can be applied to the inner surface of a microchannel wall. In some embodiments, sol-gel chemical solution deposition using methods known in the art can be employed to further increase the surface area for added interaction with particles with the walls in the laminar flow. Generally, in these embodiments, a chemical solution (sol) is used to produce an integrated network (gel). Typical organosilane precursors such as tetraethylorthosilicate (TEOS) undergo hydrolysis or a polycondensation reaction to form nanometer-sized colloids which further condensate on the surface of chemically compatible surfaces, such as silicon oxide surfaces. See e.g. Stober et al. (1968) Colloid. Interface Sci. 62:256-264, which is herein incorporated by reference.

Figure 2A:
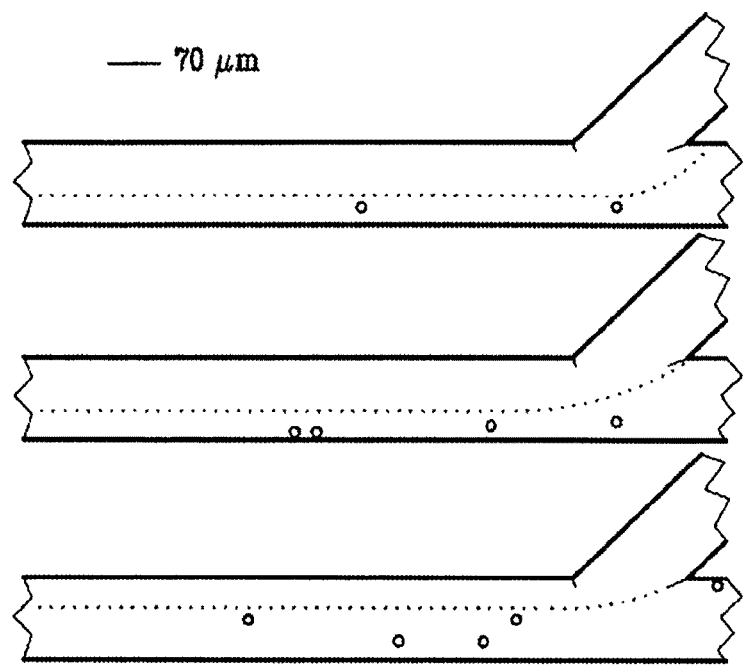
FIG. 2A shows three micrograph pictures. Each micrograph picture shows a microchannel wherein a sample fluid comprising cells was hydrodynamically focused to a virtual channel.
Figure 2B:
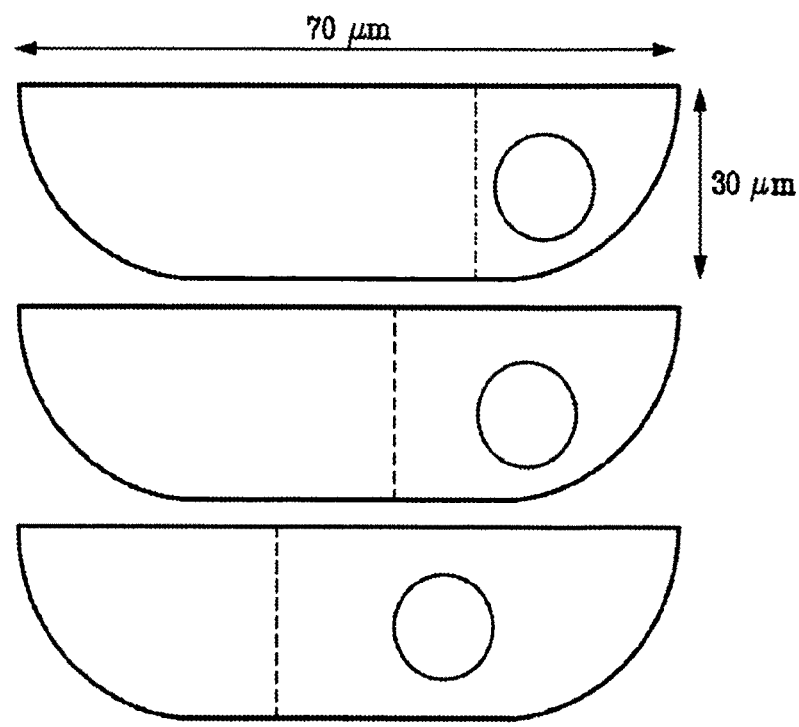
FIG. 2B schematically shows the cross sections of three different virtual channels.

FIG. 2A shows three micrographs pictures. Each micrograph picture shows a microchannel wherein a sample fluid comprising particles was hydrodynamically focused to a narrow sample flow stream. The widths of the virtual channels were controlled by the degree of hydrodynamic focusing methods known in the art, e.g. the amount of focusing fluid versus the amount of sample fluid. FIG. 2B schematically shows the cross sections of three different virtual channels. In FIG. 2B, the schematic on top shows a greater degree of hydrodynamic focusing as compared to the others. Because of the greater degree of hydrodynamic focusing, the virtual channel shown in the top schematic has a width that is narrower than virtual channels of the others.

Since the efficiency of hydrodynamic confinement is a function of the width of the cross section of a sample fluid flow, the present invention allows the efficiency of hydrodynamic confinement to be readily modified by simply changing the dimensions of the virtual channel. For example, if during the processing of a sample, one desired to increase the efficiency of hydrodynamic confinement, the width of the virtual channel is decreased by increasing the amount of the focusing fluid, decreasing the amount of the sample fluid, or both. Conversely, if one desires to decrease the efficiency of hydrodynamic confinement, the width of the virtual channel may be increased by decreasing the amount of the focusing fluid, increasing the amount of the sample fluid, or both. Thus, one need not create a new microchannel which is of a shape and size that provides the efficiency desired. In addition, the immobilized particles may be readily released from the hydrodynamic traps by increasing the pressure drop across the pore and cleared from the array. Thus, the devices of the present invention may be reused multiple times.

Various Configurations

The fluid focusing in accordance to the present invention confers more flexibility in the design of the microfluidic chips. Unlike other dynamic single-cell arrays, the hydrodynamic trapping efficiency of each particle does not solely depend on the design or configuration of the microchannels and hydrodynamic traps, but mainly depends on the extent of the fluid focusing.

Thus, according to the present invention, the dimensions of the microfluidic channels are not limited to a size that is similar to the diameter of the particle of interest (e.g. a cell=about 10 to about 30 µm). Consequently, particles that are heterogeneous in size can be readily studied from a single sample fluid without the problems of clogging and low efficiency which plague prior art methods and devices.

In addition, the ability to employ larger microchannels allows a wide variety of materials, ranging from glass to plastics, to be employed as the chip substrate. Thus, the microchannels of the present invention may be formed from any suitable substrate known in the art using methods known in the art, e.g. chemical isotropic wet-etching, anisotropic-etching, laser ablation, dry reactive ion etching, mechanical machining, imprinting, embossing and the like.

For example, channels with specific geometrical patterns in glass or quartz substrates can be fabricated by photolithography methods known in the art, e.g. the substrate surface is masked to provide a desired geometrical design then etched with an acid like hydrofluoric acid to give a D-shape channel with a constant depth and defined width. In some embodiments, substrate materials such as silicon which are amendable to anisotropic etching and dry reactive ion etching are preferred where the direction of etching is to be in the vertical dimension. Etching in the vertical dimension results in high aspect ratios of the channel and precise geometries. Plastic substrate materials such as polycarbonates, olefinic polymers, and poly(dimethlysiloxane) are preferred to create channel features using imprinting methods known in the art. Metal and ceramic substrate materials are preferred for creating channel features using laser-ablation and mechanical machining methods know in the art.

EXAMPLES OF MICROCHANNEL GEOMETRIES

Any microchannel shape or size known in the art may be used in accordance with the present invention. For example, the microchannel may have one or more rounded or flat walls. The cross section of the microchannel may be any desired shape such as a circle, square, semi-circle, elliptical, and the like. The lengthwise shape of the microchannel may be linear, curved, or have corners forming angles of desired degrees. In some embodiments, the microchannel comprising the virtual channel is straight or substantially straight. In some embodiments, the microchannel comprising the virtual channel has a shape as exemplified in the Figures provided herein.

FIG. 3A schematically shows an exemplary device configuration according to the present invention which provides efficient hydrodynamic confinement using hydrodynamic focusing. In FIG. 3A, color dyes trace the laminar flow paths in the microchannel as they converge; sample fluid containing particles of interest is subjected to fluid focusing by a focusing fluid introduced into the microchannel by way of a focusing fluid inlet port. The focusing fluid flow focuses the sample stream thereby creating a virtual channel with the particles entrained. Because of the laminar fluid flow in the virtual channel, the particles are directed towards the hydrodynamic traps for immobilization with high efficiency, since the preferred flow path for the virtual channel is through the pore ($Q_1'>Q_2'$). Once a particle is immobilized at a hydrodynamic trap, subsequent particles have no alternative but to travel through the previously higher resistive flow path $Q_2'$. The optimal flow ratio, $Q_1'>Q_2'$, for efficient immobilization is not anymore defined by combining the physical characteristics of the hydrodynamic trap for $Q_1$, e.g., diameter, and of the microchannel around the trap for $Q_2$, e.g., width, depth, as done according to methods in the prior art; but by combining the physical characteristics of the hydrodynamic trap for $Q_1'$, e.g., diameter, and of the virtual channel for $Q_2'$ defined by the fluid focusing, e.g., width, flow rate.

Thus, the present invention is able to provide efficient immobilization of particles that are heterogeneous in size. The present invention also drastically decreases the likelihood of clogging since the efficiency of the immobilization is decoupled from the physical characteristics of the microchannel around the trap. As a result, the present invention allows greater flexibility in the design of the microfluidic chip than prior art methods and devices. The unique advantage of the hydrodynamic confinement using fluid focusing design of FIG. 3A allows the use of just one focusing flow stream to efficiently trap multiple particles that are heterogeneous in size individually, sequentially and in series without clogging. In some embodiments, hydrodynamic or pressure gradient forces are generated to create the virtual channel. In alternative embodiments, however, other forces, such as acoustic, optical, magnetic, and electrical forces can be used to focus particles of a sample stream using methods known in art.

Figure 3B:
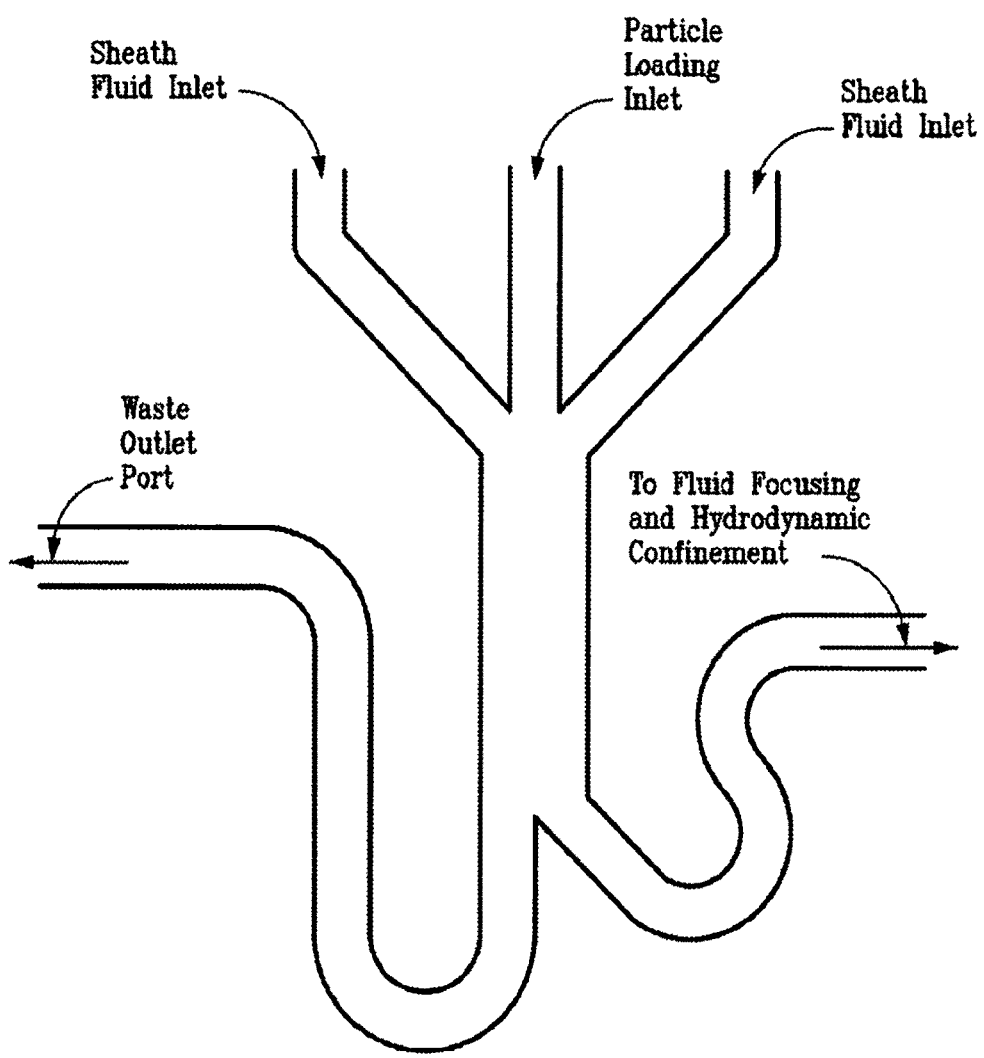
FIG. 3B schematically shows an example of a microchannel configuration for loading and sorting particles which may be employed prior to fluid focusing and hydrodynamic confinement in accordance with the present invention (e.g. placed upstream of a microchannel configuration according to FIG. 3A).
Figure 3C:
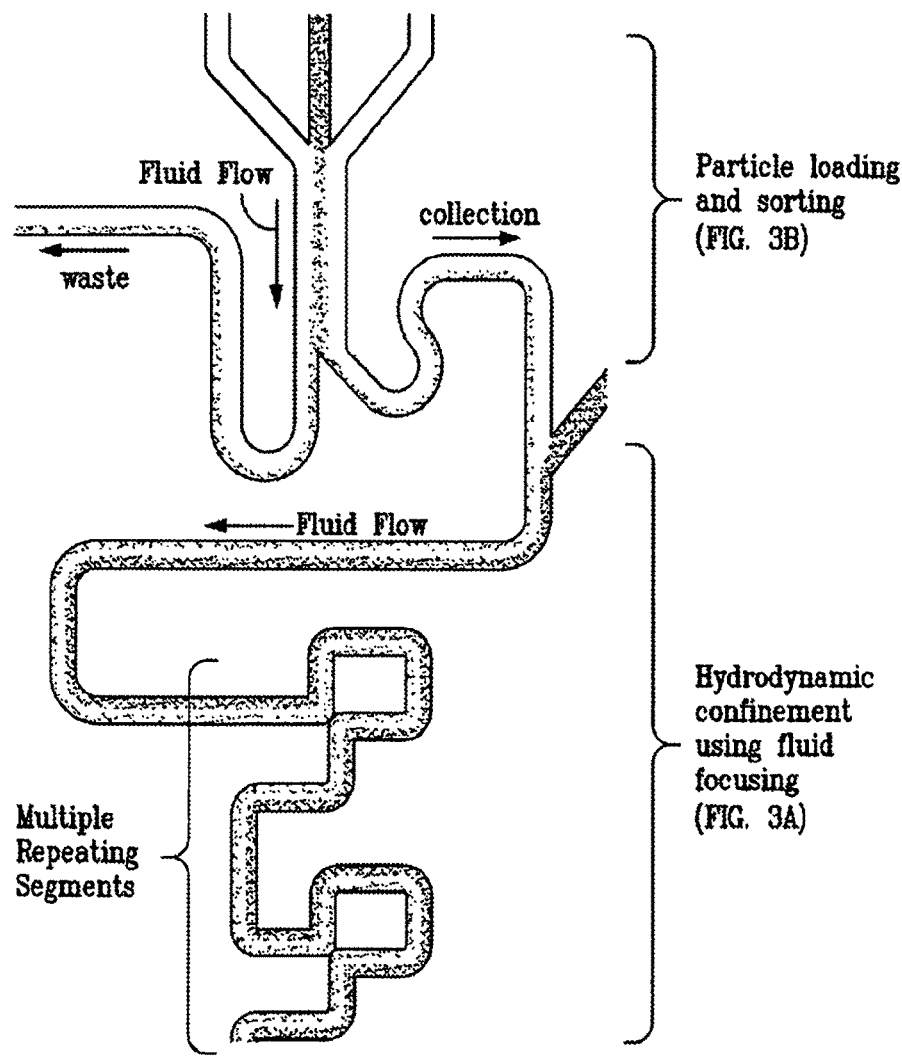
FIG. 3C schematically shows the microchannel configuration of FIG. 3B placed upstream of the microchannel configuration for hydrodynamic confinement of FIG. 3A.

Sample Loading: Upstream of the focusing fluid inlet port, the particles of interest and the sample fluid may be loaded in the microchannel using methods known in the art. The particles and the sample fluid may be loaded as a mixture at the same time. Alternatively, the particles may be loaded independent of the loading of the sample fluid. For example, as shown in FIG. 3B, a fluid containing the particles may be introduced as one fluid stream via the particle loading inlet, then individual particles of interest may be bounded to the sample fluid stream by methods known in the art, e.g. optical-based deflecting (optical tweezing), electrostatic deflection (i.e. dielectrophoreis), flow switching (valving), and the like for fluorescence-, optical absorption-, or scatter-activated particle sorting, and the like. Then the fluid, which previously contained the particles of interest, waste fluid, and sheath fluid flow to a waste outlet port and the sample fluid containing the particles of interest is subjected to fluid focusing. FIG. 3C shows the hydrodynamic traps of FIG. 3A downstream of the particle loading and sorting of FIG. 3B.

It is important to note that fluid focusing which may occur during the particle loading and sorting stage (e.g. FIG. 3B) as a result of the introduction of sheath fluid in order to align the particles to flow in a narrow stream (e.g. single file) should not be confused with the fluid focusing a focusing fluid during the hydrodynamic confinement stage (e.g. FIG. 3A). Fluid focusing during particle loading and sorting does not result in a virtual channel in a microchannel where the flow of the virtual channel is directed towards a hydrodynamic trap (see e.g. the $Q_1'$ flow path exemplified in FIG. 1B) in the microchannel such that a particle in the focused flow becomes trapped in the hydrodynamic trap.

EXAMPLES OF HYDRODYNAMIC TRAPS

Figure 4:
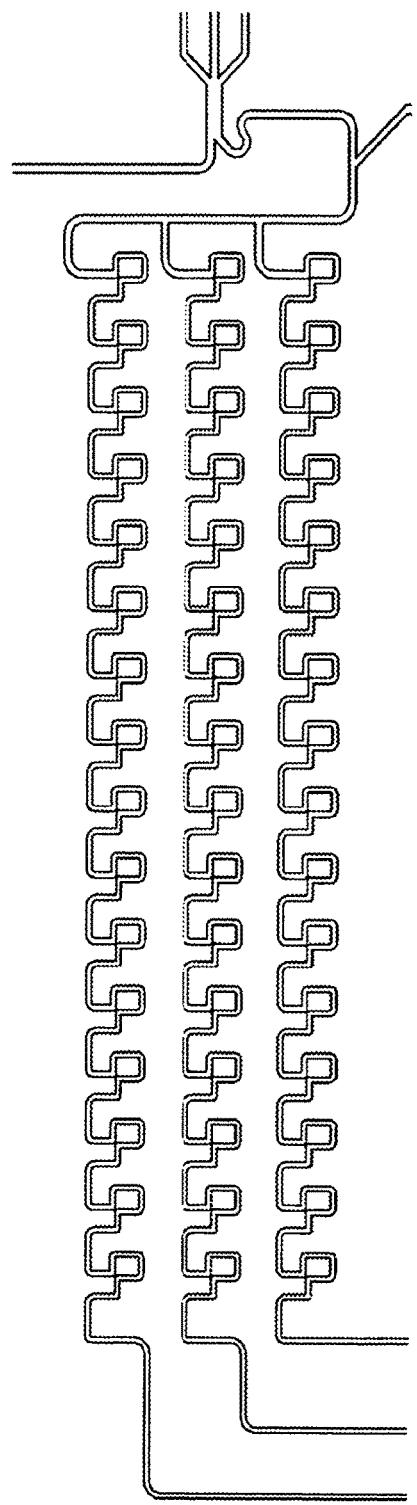
FIG. 4 schematically shows three sets of hydrodynamic traps in parallel.

In FIG. 3A, downstream of the focusing fluid inlet port is a set of hydrodynamic traps in series. In some embodiments, a set of hydrodynamic traps is 1 to about 25 hydrodynamic traps, preferably about 5 to about 20 hydrodynamic traps, more preferably about 12 to about 16 hydrodynamic traps. The hydrodynamic traps of a set may be the same or different, e.g. the dimensions in channel length or trap size may be the same or different. In addition, the channel sections prior to each hydrodynamic trap in a set may be the same or different, e.g. the channel prior to one trap may be substantially linear and the channel section prior to the next trap may have one or more turns. A device according to the present invention may comprise one or more sets of hydrodynamic traps, which sets are arranged in parallel as shown in FIG. 4.

Figure 5A:
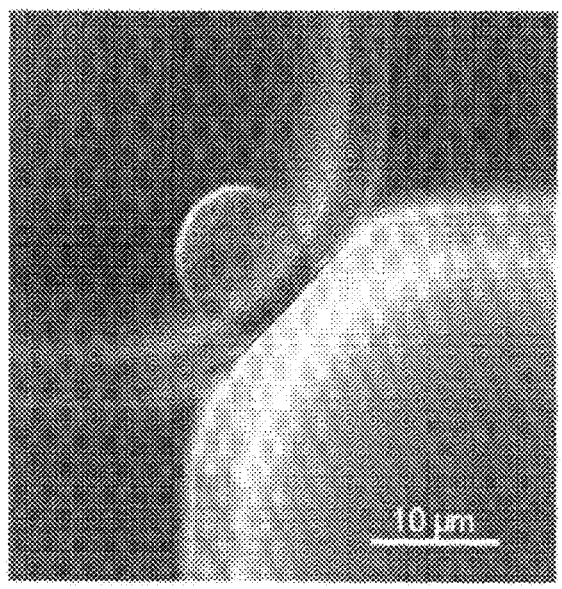
FIG. 5A is a micrograph of a cell which was immobilized in the hydrodynamic trap in accordance with the present invention.

FIG. 5A shows a particle (cell) immobilized in a hydrodynamic trap. Generally, the cavity of a hydrodynamic trap has a radius similar to the diameter of the particle to be trapped and the width of the pore or small channel is smaller than the diameter of the particle. The hydrodynamic traps of the present invention may be of any suitable shape and size known in the art which provides a flow ratio of $Q_1'>Q_2'$ for a given virtual channel $Q_2'$ defined by fluid focusing.

Figure 5B:
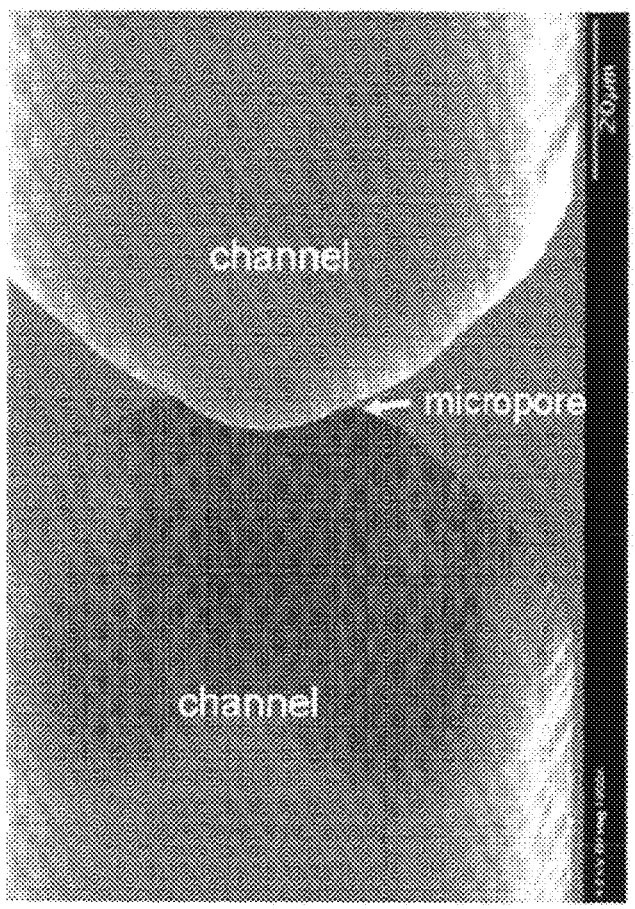
FIG. 5B is a SEM micrograph angled at 40° of an example of a hydrodynamic trap having a micropore. For imaging purposes, only half of the hydrodynamic trap is shown.

In some embodiments, semi-elliptical hydrodynamic traps are created with a single overlapping chemical wet-etch front as illustrated in FIG. 5B. The hydrodynamic trap illustrated in FIG. 5B, the embedded micropore was fabricated using single-level isotropic wet etching in glass according to methods known in the art to create pores features with different depths within the microchannels. See e.g. Perroud et al. (2009) Lab on a Chip, DOI: 10.1039/B817285D, which is herein incorporated by reference. Two overlapping etch fronts result in an opening. In some embodiments, two wet-etched fronts overlap by about 58 µm give a micropore having a size of about 20 µm wide and about 6 µm deep for a depth of 30 µm for the microchannel. The overlap can range maximum of 62 µm to a minimum of 45 µm for an effective pore.

Other methods and materials known in the art may be employed to create hydrodynamic traps to be used in accordance with the present invention. For example, in some embodiments, the hydrodynamic traps according to the present invention are fine slits produced by laser ablation which results in relatively high aspect ratio features. Ablated slits having dimensions of about 5 µm wide and about 15 µm deep and greater are possible. See Tseng et al. (2004) Optics and Lasers in Engineering 41(6):927-847, which is herein incorporated by reference. In some embodiments, the methods and devices of the present invention employ micropores in polymer substrates such as polycarbonate, cyclic olefins, and other thermosettable resins made by methods known in the art such as nanoimprint lithography. See Chou et al. (1996) J of Vacuum Science and Technology B 14(6):4129-4133, which is herein incorporated by reference.

Additional Fluid Focusing

Figure 6:
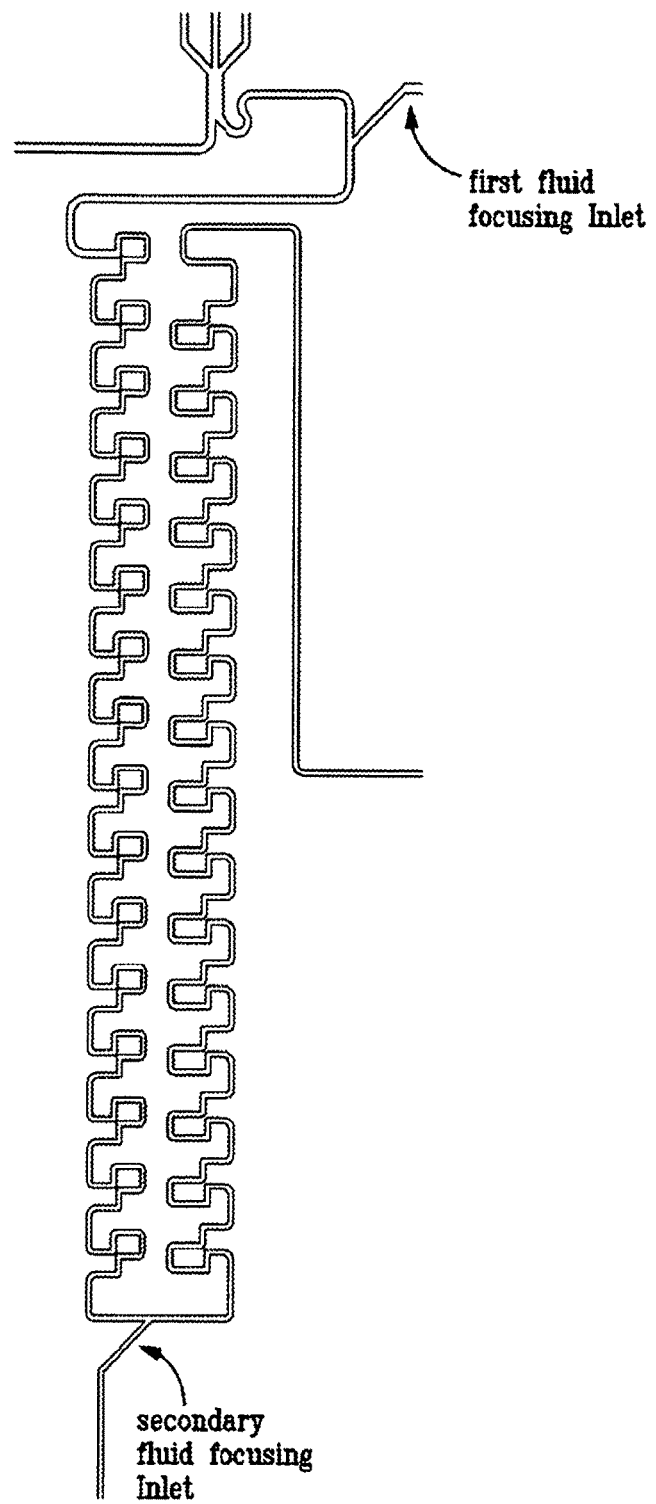
FIG. 6 schematically shows secondary fluid focusing between two sets of hydrodynamic traps in series.

In addition to the initial fluid focusing which creates the virtual channel, secondary fluid focusing may be applied downstream to maintain or change the dimensions of the virtual channel or even add one or more additional virtual channels of the same or different sample fluids as in the case of branching points for multiple arrays connected in an expanding fashion. As shown in FIG. 6, the secondary fluid focusing may be applied between hydrodynamic traps of a set of hydrodynamic traps or the secondary fluid focusing may be applied between two sets of hydrodynamic traps, or both.

The additional fluid focusing may be the same or different than the initial fluid focusing. For example, if the initial fluid focusing is by hydrodynamic focusing, the secondary fluid focusing may be by hydrodynamic focusing or electrokinetically driven focusing. In addition, the focusing fluid of the secondary fluid focusing may be the same or different than that of the initial focusing fluid. Similarly, if more than one secondary fluid focusing is applied, the secondary fluid focusing, the secondary focusing fluid, or both, may be the same or different.

Enhanced Immobilization

In some embodiments, the retention or immobilization of a particle at a hydrodynamic trap may be increased or made permanent by comprising a trapping agent which binds or retains the particle after the initial trapping. Such a trapping agent may provide covalent, ionic or hydrogen bonding, electrical or magnetic attraction, hydrophobic/hydrophilic interactions, or the like with the particle. Examples of suitable trapping agents include antibodies, receptors, ligands, magnetic particles, functionalized surfaces, chemical coatings, and the like. In these embodiments, the trapped particle will remain in the trap when the fluid flow is stopped or the pressure gradient is reduced to zero or is reversed. One approach is to modify the surface in the vicinity of the trap using methods known in the art such as surface grafting reactions with silane chemistry. For example, glass can be functionalized by absorbing a receptor compound to bind its corresponding ligand. See e.g. Garcia et al. (2006) Biomedical Materials Research 40(1):48-56, which is herein incorporated by reference. In some embodiments, for particles which are magnetic or electrical polarizable, the pressure which initially traps the particle in a hydrodynamic trap can be enhanced or even negated with magnetic or electrical fields.

EXAMPLES OF APPLICATIONS

The present invention allows individual particles, such as single cells, to be loaded in a manner such that the position of each individual particle can be correlated to time and order. Thus, the present invention allows the study of cell-cell interactions and communication.

The present invention is not limited to enrichment of rare cells, single-cell imaging, or cell-to-cell communication studies, but can also be applied for bead-based chemical microarrays, where beads have specific chemistry to capture biomolecules from solution or recently released from cells.

Since the average shear stress experienced by individual particles in the hydrodynamic traps can be precisely controlled by varying the extent of hydrodynamic focusing, the mechanical properties, such as dynamical deformation and cell hemolysis, of particles can be studied on a micrometer scale.

For example, cell partially extruded through pores can be monitored through chemical assays to asses the state of health, life expectancy, the rate of recovery due to a stressful environment.

Compatibility with Other Methods and Devices

Because the fluid focusing in accordance with the present invention allows flexibility and more choices of substrate materials, machining methods, and microchannel geometries that are suitable for efficient hydrodynamic confinement, the methods and devices of the present invention may be readily integrated or complexed with other microfluidic methods and devices, such as particle sorting and optical tweezing, microscopy, and the like to achieve unforeseen advantages.

For example, integration of a cell sorter with fluid focusing and hydrodynamic confinement in accordance with the present invention provides the following advantages: (1) a particular subpopulation of particles or cells can be isolated from a heterogeneous sample, (2) particles or cells of particular interest may be readily screen and selected to be those making up the particle/cell array (immobilized in the hydrodynamic traps), (3) neighboring particles or cells on the array can be precisely controlled to study particle interactions such as inter- or intracellular communication, and (4) the particles or cells of interest can be introduced in the array at given time intervals such that a given position (hydrodynamic trap) can be translated to a given time period, e.g. age of a cell, incubation period, reaction time, and the like.

For example, an optical cell sorter, such as that described by Tu et al. can be integrated with the methods and devices of the present invention. See Tu et al. (2004) Proceedings of SPIE—Internat'l Society for Optical Engineering 5514:774-785, and Wang et al. (2005) Nature Biotech. 23:83-87, and Perroud et al. (2008) Anal. Chem. 80:6365-6372 which are herein incorporated by reference. Briefly, cells were hydrodynamically focused using methods known in the art into a single file to achieve high detection efficiency in the subsequent interrogation region. In this region, the presence of a cell was detected through forward-scattering and laser-induced fluorescence (LIF) was used to assay cells for a particular protein of interest. Both scattering and fluorescent signals of a cell passing through the interrogation region trigger and activate an acousto-optical modulator (AOM) to raster the near-infrared laser in the deflecting region. Cells captured by the laser in that region were then trapped and deflected into a laminar flow stream (fluid sample stream) for downstream binning. Then the fluid sample containing the particle of interest was subjected to fluid focusing and hydrodynamic confinement according to the present invention.

Application of µFACS and SCA

In some embodiments, the present invention provides a micro-fluorescence-activated cell sorter (µFACS) integrated in tandem with at least one single cell (or particle) array (SCA). In these embodiments, the individual cells or particles are immobilized in the traps by hydrodynamic confinement using fluid focusing as described herein. The tandem arrangement of a µFACS and an SCA allows the analysis of a given subpopulation of cells or particles from a sample having a mixture of different cells or particles. µFACS is capable of rapid, multi-parametric measurements on large cell populations; whereas, microscopy imaging can provide spatial information at high-resolution, but only on a limited number of cells. µFACS and hydrodynamic confinement according to the present invention are fundamentally different, but the integration of the two into a single multiplexed assay is powerful approach to studying cellular systems.

In particular, as disclosed herein, the tandem integration of μFACS and SCA allowed analysis of the signaling pathways associated with host-pathogen responses for a select population of macrophage cells. To achieve this, on-chip flow cytometry was coupled with noninvasive optical cell sorting to select representative cells and register them into downstream single-cell traps for high-resolution imaging.

Microfluidic chips were custom-fabricated using wet-etching and photolithographic methods known in the art. Specific to the process, microchannels were isotropically etched in 0.75-mm-thick fused-silica base wafers. Fluid access holes (0.5 mm dia.) were drilled into a cover wafer before being visually aligned and thermally bonded to the base wafer. A Delrin polymer microfluidic manifold with integrated O-ring seals provided the interface between the chip and fluid reservoirs. To be compatible with a large numerical aperture (NA) microscope objective (≥1.4), the base wafer was polished to a final thickness of 170 μm using a proprietary lapping-polishing process (GM Associates). The removal of 530 μm of material from the base wafer left low levels of subsurface damages (commercial grade finish 80/50 scratch/dig), with a surface roughness of about 2 micro-inch. Prior to each use, the channels were coated with a 4% bovine serum albumin solution to prevent particle or cell adhesion to the walls.

Fluid was delivered to each port of the manifold through 1/32" O.D. 0.005" I.D. PEEK tubing (Upchurch Scientific, Oak Harbor, Wash.) and swaged in place with 1/32" TubeTite fittings (Labsmith, Livermore, Calif.). 2.0 ml screw-cap microcentrifuge tubes (89004-302; VWR, West Chester, Pa.) fitted with custom-machined caps served as fluid reservoirs. The caps have two ports to allow the delivery of $N_2$ gas to pressurize the headspace in the vial and push the fluid through a PEEK tube placed below the liquid level into the chip. All four fluid reservoirs were pressurized by individual electronic pressure control units (VSO-EP; Parker, Cleveland, Ohio) to ensure precise control of hydrodynamic focusing, cell velocity, and cell positioning.

Figure 7:
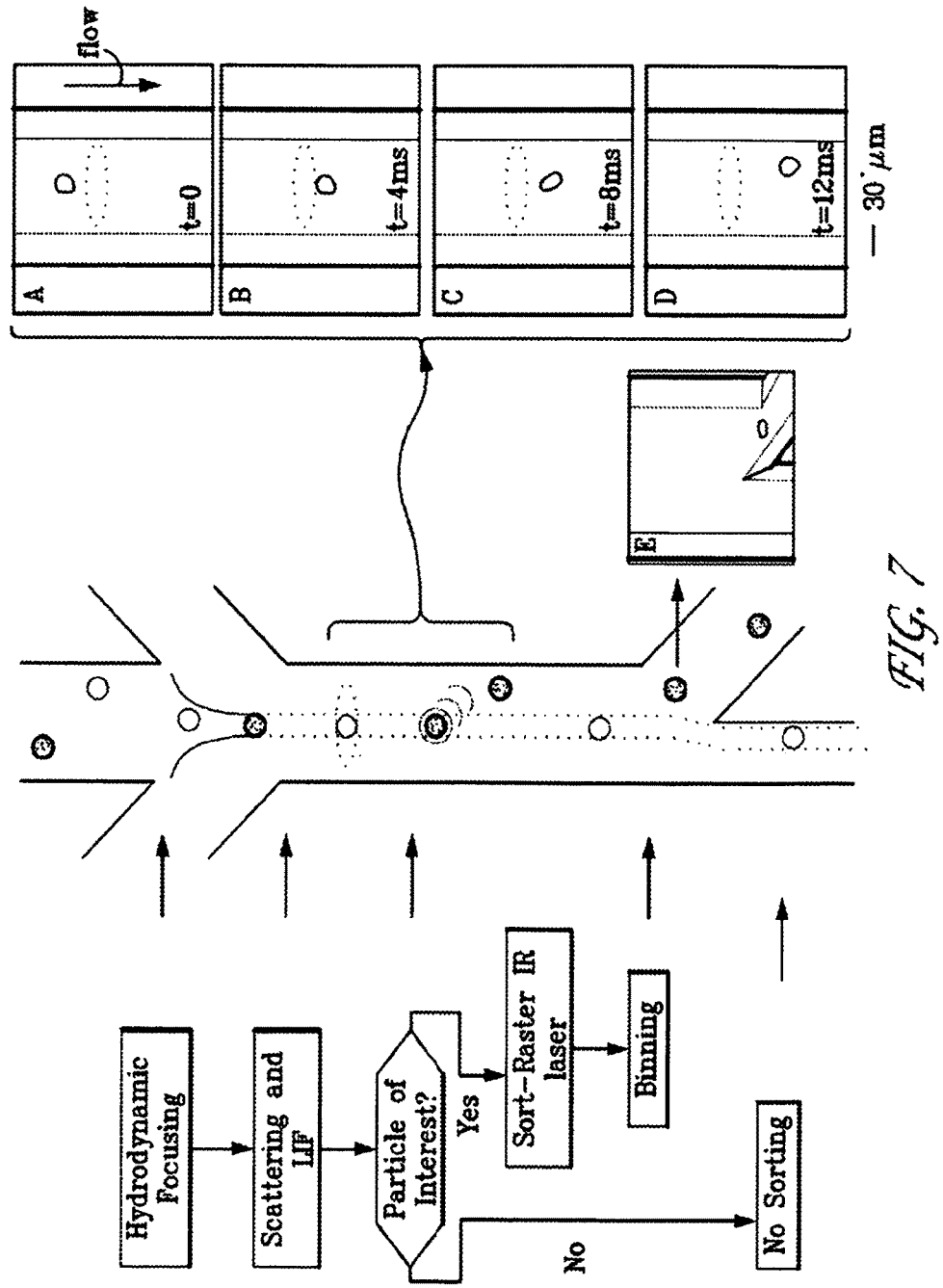
FIG. 7 illustrates the sorting and binning of macrophages based on optical forces which may be conducted prior to hydrodynamic confinement, such as in FIG. 3B.

For flow cytometry, a center fluid stream containing RAW 264.7 mouse macrophage cells were focused to a width of 10 μm by two neighboring sheath flows (velocity of about 20 mm/s) using methods known in the art. Macrophages were detected and characterized by forward-scattering and laser-induced fluorescence (red and green) using methods known in the art. The fluorescence signals triggered a powerful (about 9.6 W at the sample) 1064-nm laser, which optically deflected cells of interest from the center of the channel into a neighboring (sample) fluid flow stream. This optical tweezing laterally displace the cells by about 30 μm into the sample flow stream. See FIG. 7. The laminar nature of microfluidic flow ensures that the sorted cells will stay on the flow path of the sample fluid and be directed into a collection channel, where fluid focusing, in accordance with the present invention, focuses the cells against a given channel wall. The cells were then individually trapped in a series of hydrodynamic traps using methods known in the art. Then the viability of the trapped cells were assessed by epifluorescent imaging using 1 μM calcein AM fluorescent stain according to methods known in the art. See Perroud et al. (2008) Anal. Chem. 80:6365-6372, which is herein incorporated by reference.

Figure 8:
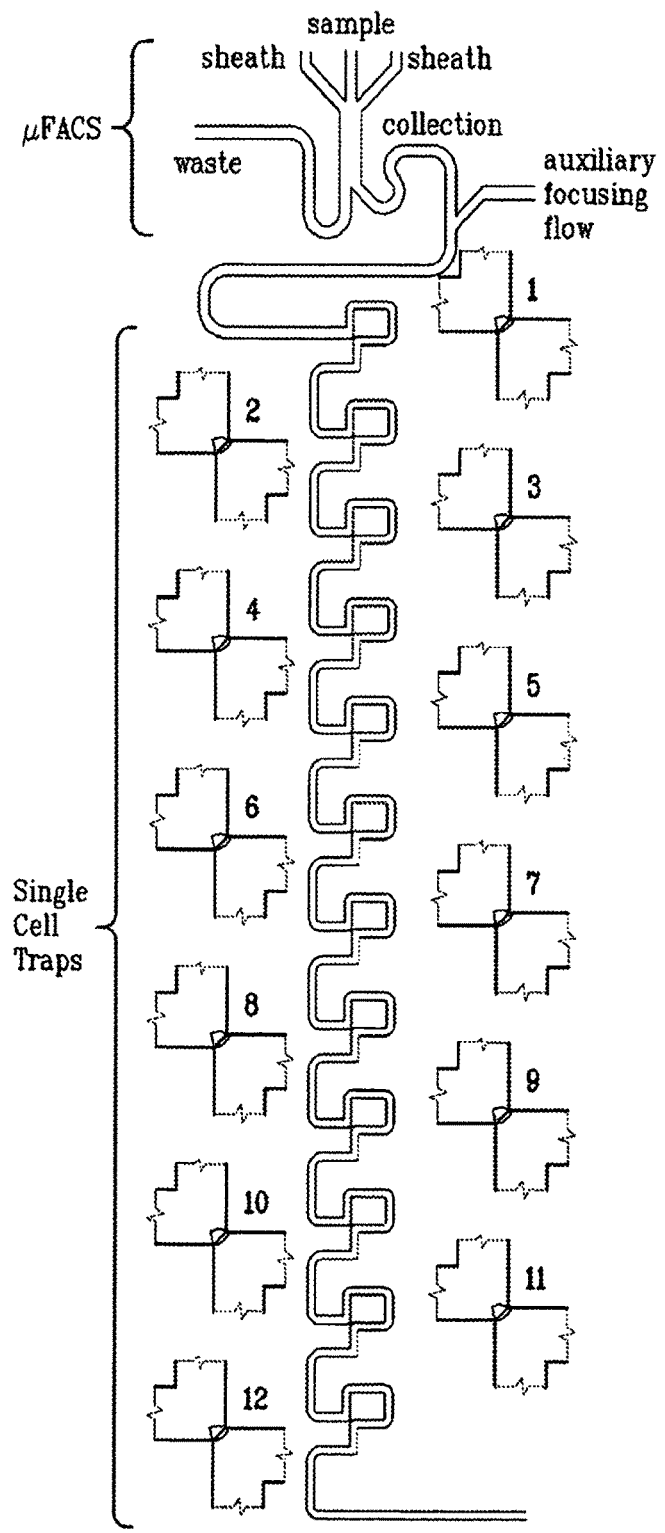
FIG. 8 schematically shows the tandem integration of microfluidic-based fluorescence activated cell sorter (µFACS) with a 12-trap single cell array (SCA). Inset
Figure 9:
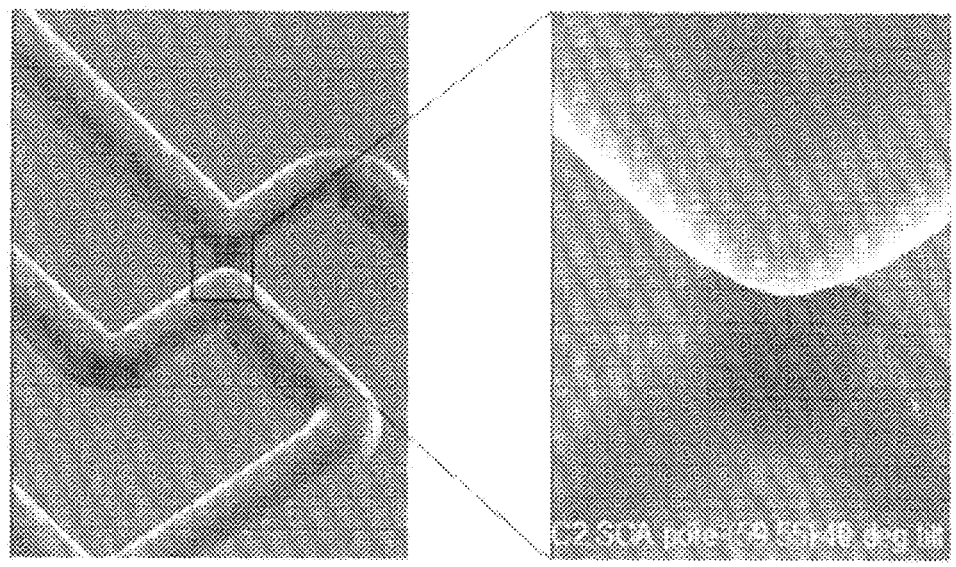
Figure 10A:
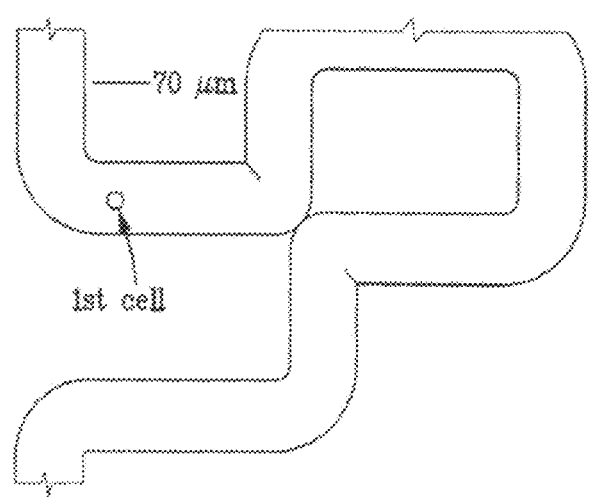
FIGS. 10A-10D are micrographs that show that there is no particle (cell) trapping without fluid focusing of the sample fluid.
Figure 10B:
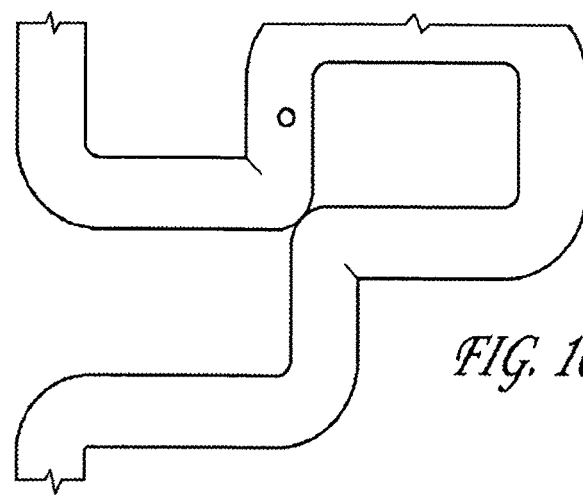
Figure 10C:
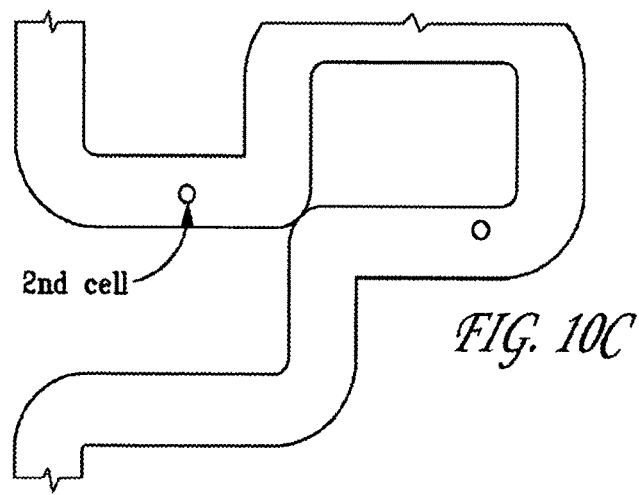
Figure 10D:
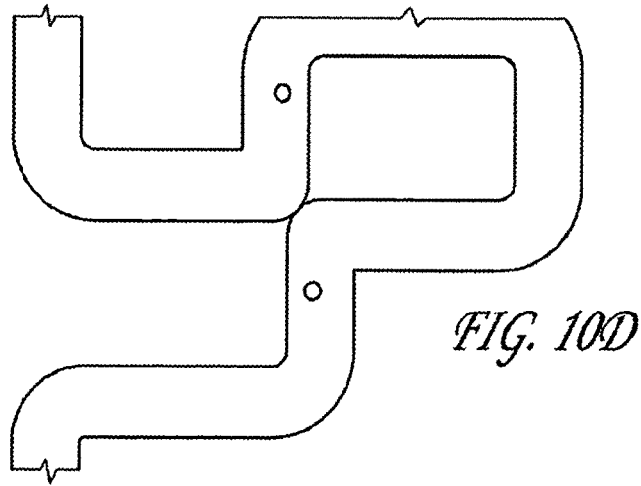

An exemplary design of the μFACS and SCA device of the present invention is shown in FIG. 8. For each hydrodynamic trap (12 total), the pore was about 26 μm wide by about 7 μm deep which was formed at each junction of the microchannel corners using a previously described method. See Perroud et al. (2009) Lab on a Chip, DOI: 10.1039/B817285D, which is herein incorporated by reference, see also FIG. 9.

Since the height of the pore (7 μm) is smaller than the 15 μm diameter macrophage, it acts as a trapping site and immobilizes the cell for microscopy imaging. In addition, the channel geometry was designed such that the initial flow path for the fluid in the channel is through the pore because it has the lowest fluidic resistance. The ratio between the two flow paths ($Q_1 > Q_2$) is about 4. Once the pore is occupied by a cell, the plug dramatically increases the fluidic resistance and redirects the next sorted cell around the bend and towards the next trap. In this configuration, each cell is trapped sequentially (starting from the closest trap to the sorter) with about 100% trapping efficiency.

Figure 11A:
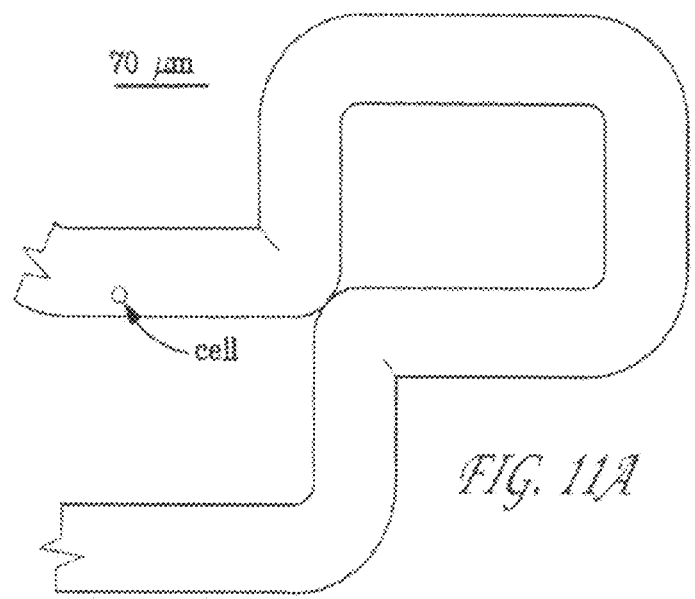
FIG. 11A shows a single cell (particle) moving towards a hydrodynamic trap after fluid focusing according to the present invention.
Figure 11B:
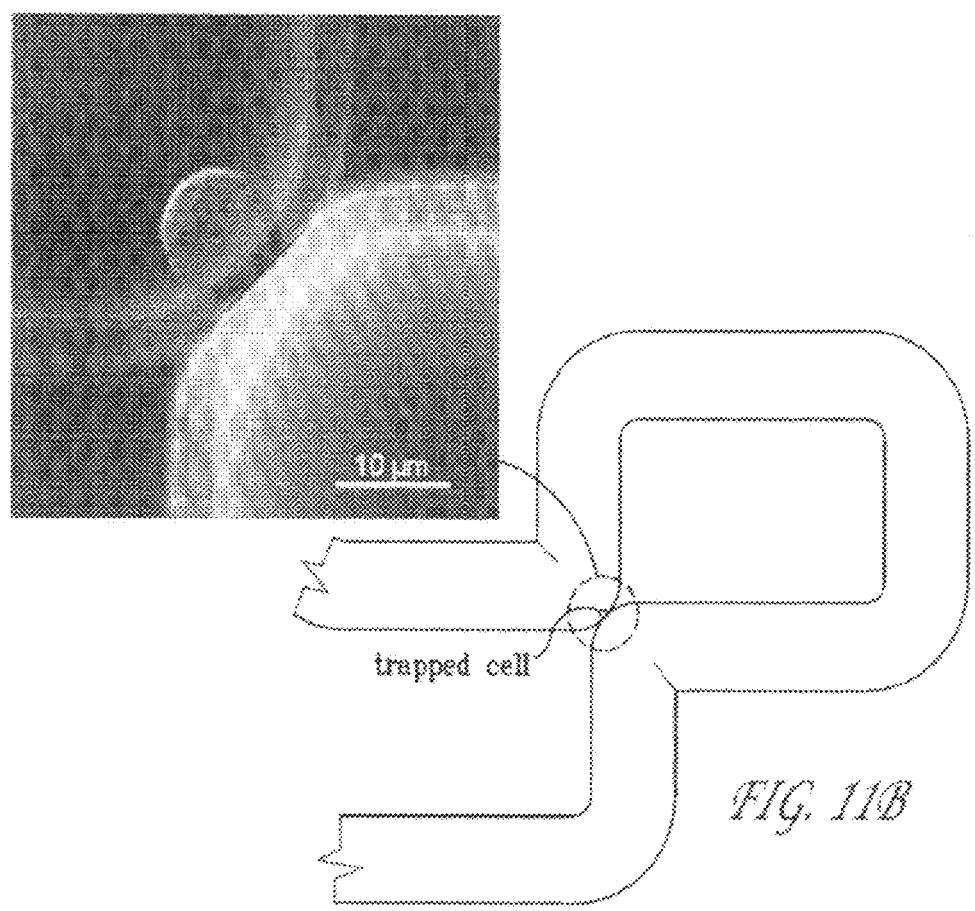
FIG. 11B shows the single cell of FIG. 11A trapped in the hydrodynamic trap and the inset is a micrograph of the trapped cell.

Without fluid focusing of the sample fluid, cells located traveling in the middle of the microfluidic channel will not get trapped at the pore and will instead continue down the main channel. See FIGS. 10A-10D. As a result of fluid focusing the sample fluid, the cell travels along the microchannel wall where it will be captured and immobilized at the pore. See FIGS. 11A and 11B.

Figure 12:
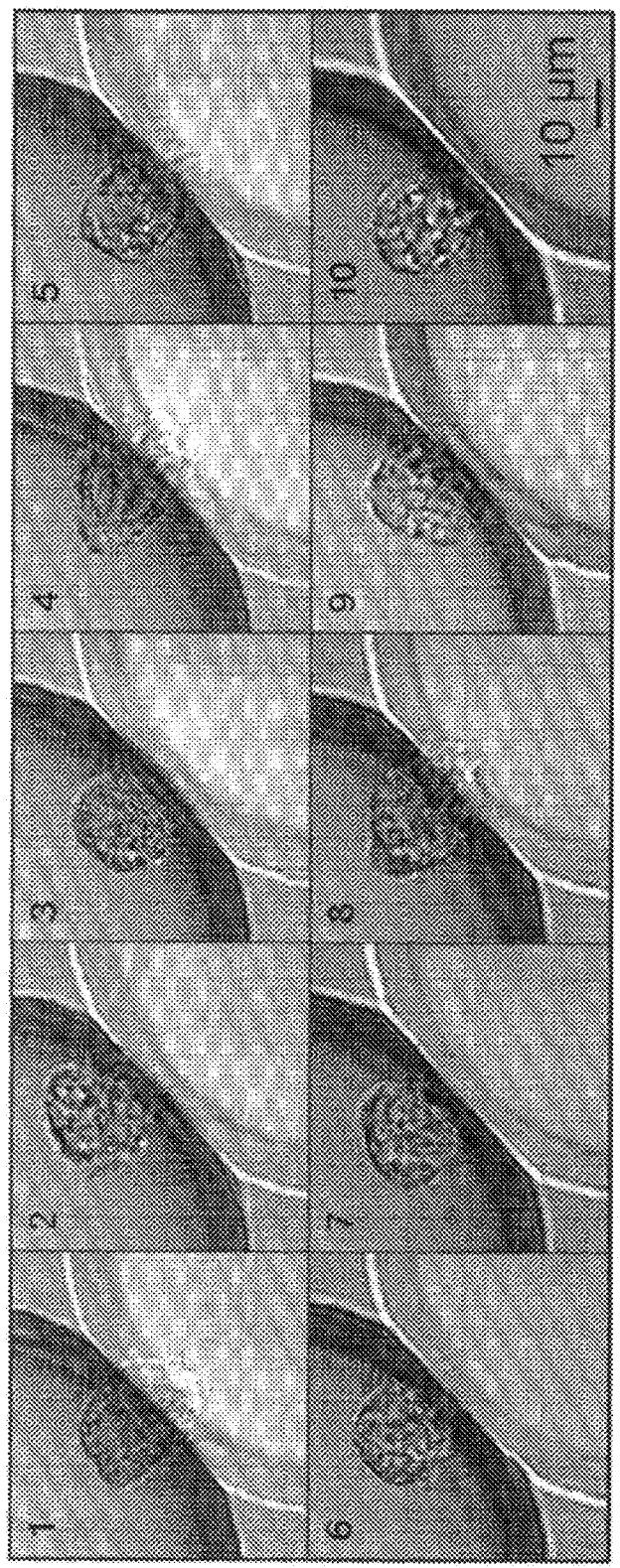

FIG. 12 is a compilation of images from 12 sequential traps. Cells at a concentration of $4 \times 10^6$ cells/ml were detected in a single-file manner by an optical detector and selected for hydrodynamic confinement. Selected cells were loaded into each trap in a sequential fashion. Each macrophage cells was monitored for viability using a commercial live-dead staining assay (Calcein AM) fluorescent stain. An external temperature controller maintained the temperature inside the chip at 37° C. In addition, very low flow rate (e.g. 100 nl/min.) provided fresh growth media to cells in the traps. Each macrophage cells trapped at the pores were viable and showed no change in morphology after about 4 hours as shown in the images in FIG. 12. Thus, the μFACS and SCA of the present invention allow long time course measurements of cellular events. To achieve long-term viability, nutrient media may be provided to the immobilized cells using methods known in the art.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A microfluidic device which comprises at least one microchannel having at least one hydrodynamic trap, at least one focusing fluid inlet, said focusing fluid inlet is upstream of the hydrodynamic trap such that a focusing fluid introduced therein results in a virtual channel of a sample fluid and a vitual channel of a focusing fluid wherein, when present, both virtual channels preferentially flow directly adjacent to the at least one hydrodynamic trap.

2. The microfluidic device of claim 1, which comprises at least one set of hydrodynamic traps.

3. The microfluidic device of claim 2, which comprises two or more sets of hydrodynamic traps in series.

4. The microfluidic device of claim 2, which comprises two or more sets of hydrodynamic traps in parallel.

5. The microfluidic device according to claim 1, which further comprises at least one secondary fluid inlet.

6. The microfluidic device according to claim 1, wherein one or more of the hydrodynamic traps have a trapping agent which may be the same or different.

7. The microfluidic device according to claim 1, wherein an effective area of cross-section of the virtual channel is about 5 fold to about 20 fold larger than a cross-sectional area of a particle of interest introduced into the microchannel.

8. The microfluidic device according to claim 1, wherein prior to the hydrodynamic trap being occupied by a particle of interest, a ratio of a flow rate of a flow path through the hydrodynamic trap to a flow rate of a flow path around the hydrodynamic trap is configured to be about 3 to about 4.

* * * * *